United States Patent
Mahant et al.

(10) Patent No.: US 7,736,888 B2
(45) Date of Patent: *Jun. 15, 2010

(54) STAGE AND PLATFORM FOR BUILDING A BIOCHIP AND BIOCHIP

(75) Inventors: Vijay K. Mahant, Murrieta, CA (US); Fareed Kureshy, Del Mar, CA (US)

(73) Assignee: Autogenomics, Inc., Carlsbad, CA (US)

( * ) Notice: Subject to any disclaimer, the term of this patent is extended or adjusted under 35 U.S.C. 154(b) by 1527 days.

This patent is subject to a terminal disclaimer.

(21) Appl. No.: 10/346,879

(22) Filed: Jan. 17, 2003

(65) Prior Publication Data

US 2004/0005697 A1 Jan. 8, 2004

Related U.S. Application Data

(63) Continuation-in-part of application No. 09/735,402, filed on Dec. 12, 2000, now abandoned.

(51) Int. Cl.
*C12M 1/00* (2006.01)
*C12M 1/34* (2006.01)
*C12M 3/00* (2006.01)
*C12Q 1/68* (2006.01)

(52) U.S. Cl. .............. 435/283.1; 435/6; 435/287.1; 435/287.2

(58) Field of Classification Search ............. 435/6, 435/283.1, 287.1, 287.2
See application file for complete search history.

(56) References Cited

U.S. PATENT DOCUMENTS

| | | | | |
|---|---|---|---|---|
| 3,980,540 A | * | 9/1976 | Hoefer | 204/467 |
| 4,587,102 A | * | 5/1986 | Nagatomo et al. | 422/56 |
| 5,250,443 A | * | 10/1993 | Lindholm et al. | 436/529 |
| 5,418,136 A | * | 5/1995 | Miller et al. | 435/5 |
| 5,455,344 A | * | 10/1995 | Harper et al. | 536/123.1 |
| 5,601,959 A | * | 2/1997 | Brault et al. | 430/126 |
| 5,691,152 A | * | 11/1997 | Burton et al. | 435/7.5 |
| 5,728,994 A | * | 3/1998 | Hutton | 219/121.69 |
| 5,776,643 A | * | 7/1998 | Hirai | 430/7 |
| 5,807,522 A | * | 9/1998 | Brown et al. | 422/50 |
| 6,287,874 B1 | * | 9/2001 | Hefti | 436/501 |

OTHER PUBLICATIONS

Yang et al, J. Appl. Polymer Sci., vol. 92, pp. 3201-3210 (2004).*
The definition of "fluorescence" provided by the online dictionary at merriam-webster.com.*
The definition of "or" provided by the online dictionary at merriam-webster.com.*

* cited by examiner

*Primary Examiner*—Robert T. Crow
(74) *Attorney, Agent, or Firm*—Fish & Associates, PC

(57) ABSTRACT

A biochip, a platform which composes the biochip, and a stage which composes the platform. The biochip is for detecting analytes in a test sample. The platform comprises a stage. The stage of the invention includes a carrier.

20 Claims, 6 Drawing Sheets

STAGE AND PLATFORM FOR BUILDING A BIOCHIP AND BIOCHIP

This application is a continuation-in-part of U.S. patent application Ser. No. 09/735,402, which was filed Dec. 12, 2000, now abandoned.

BACKGROUND OF THE INVENTION

1. Field of the Invention

The present invention relates to devices and methods for detecting and analyzing nucleic acids, proteins, macromolecules and other haptens. In particular, the invention includes a biochip. The invention is further directed to devices which the biochip comprises. Methods for making and using biochips and the devices which compose the biochip are also subjects of the present invention.

2. Background of the Invention

Nucleic acid probe technology has application in detection of genetic mutations and related mechanisms, cancer screening, determining drug toxicity levels, detection of genetic disorders, detection of infectious disease and genetic fingerprinting. Nucleic acid-based probe methods offer several advantages over conventional microbiological or immunological methods for detection of organisms, as described by Nakamura and Bylund (J. Clinical Laboratory Analysis, 6, 73-83, 1992). Utilizing biochip or microarray technology, one can conduct massively parallel experiments in the areas of genetics and proteomics in applications as diverse as pharmacogenomics, gene expression, compound screening, toxicology, Single Nucleotide Polymorphism (SNPs) analysis, Short Tandem Repeats (STRs) and molecular diagnostics.

Methods to amplify the number of copies of the nucleic acid available for detection of the signal generated after hybridization of the nucleic acid probe have been utilized. A review of nucleic acid based detection methods and various amplification schemes such as polymerase chain reaction (PCR), ligase chain reaction (LCR), transcription based amplification, cycling probe reaction, Q.beta. replicase, and strand displacement amplification may be found in M. J. Wolcott, Clinical Microbiology Reviews, 5, Oct. 1992, pp 370-386.

U.S. Pat. No. 5,175,270 describes an amplification reagent consisting of layers of nucleotide polymers containing double stranded and single stranded sections. Each section has an end which is capable of hybridizing with another molecule.

Probe or hybridization assays are often based on the attachment of an oligonucleotide probe to a surface in order to capture a target nucleic acid molecule (analyte) from a sample. The attachment of this probe to the surface may be through covalent bonds or through a variety of passive absorption mechanisms (e.g., hydrophobic or ionic interactions).

U.S. Pat. No. 5,279,955 describes an immobilization process which uses a heterofunctional cross-linker for a plastic support. The cross-linker consists of a central ring which is hydrophobic and interacts with the plastic, and a hydrophilic chain which terminates in a group capable of reacting with a nucleic acid. Covalent attachment is achieved through a succinyl-olivetol-N-hydroxysuccinimide.

U.S. Pat. No. 5,262,297 describes immobilization of a probe through copolymers which contain reactive carboxylic acid groups and an 8-50 atom spacer with two or more unsaturated groups within the spacer.

U.S. Pat. No. 5,034,428 describes an immobilization process for probes in which a monomer is joined onto a hydrophilic solid support which can be irradiated in an oxygen free atmosphere. This method provides for covalent attachment of the probe.

U.S. Pat. No. 4,806,546 also describes an immobilization process for an amide modified nylon. The method relies on an amidine linkage under anhydrous conditions in the presence of an alkylating agent.

Maskos and Southern, 20 Nucleic Acid Research 1679, 1992, describe a linker system for the attachment of a nucleic acid to a glass support. The linker system allows for the chemical synthesis of a strand of nucleic acids on the surface. The primary advantage of the linker is that it is stable to an ammonia treatment which is required in the synthesis of the polynucleotide. A hexaethylene glycol spacer is incorporated into the linker which attaches to the glass through a glycidoxypropyl silane which terminates in a primary hydroxy group. The silane is condensed onto silane groups on a solid support. Additional cross-linking may be obtained by introducing water so that the epoxide group is cleaved to a diol. An acidic solution facilitates this process. The length of the linker may be varied by changing the spacer to ethylene glycol, pentaethylene glycol, etc.

Nucleic acid probes that have hybridized to their target sequence are detected based on various methods that introduce a detectable chemiluminescent, fluorescent or other identifiable label into a nucleic acid probe. Several of these techniques, are described in U.S. Pat. Nos. 4,968,602, 4,818,680, 5,104,791, and 5,272,056, and International applications W091/00926 and GB2169403A.

U.S. Pat. No. 5,283,174 (Arnold et al.), describes the use of a chemiluminescent label with DNA probes. The label is composed of an acridinium ester and has a number of desirable properties. It is stable to hybridization conditions, light is emitted only upon exposure to an alkaline peroxide, the emission kinetics are rapid, and the label on the unhybridized probe can be destroyed without an impact on the signal generated by the hybridized probe.

U.S. Pat. No. 5,089,387 describes a diffraction assay for the detection of DNA hybridization. In this invention, a solid support, generally silicon or polysilicon, is coated with a DNA probe. These surfaces are required to inherently adhere the DNA probe to the surface. Once the surface is coated with the probe, the surface is selectively inactivated to provide a series of very strictly controlled reactive probe lines for the generation of the diffraction grating. The unreacted surface is required to be non-light disturbing. The diffraction grating is only generated upon the addition of the analyte to the surface. The angle of diffraction is a function of the wavelength of incident light and the density and spacing of the individual gratings on the surface. A single detector or a multiple detector array may be used to detect and measure the light from all desired orders of the diffracted light.

U.S. Pat. No. 6,060,237 describes a light reflecting assay for the detection of nucleic acid hybridization. In the invention, an optically active solid support capable of producing a thin film effect is coated with an amplifying probe reagent able to bind to the target nucleic acid and create an increase in mass change on the optically active surface without disrupting the thin film effect. The direct optical thin film detection methods of the invention are extremely sensitive to changes in mass at the surface of the optically active support.

Mixed phase systems have typically been used to perform hybridization assays. In mixed phase assays the hybridizations are performed on a solid phase such as nylon or nitrocellulose membranes. For example, the assays usually involve loading a membrane with a sample, denaturing the DNA or creating single stranded molecules, fixing the DNA or RNA to the membrane, and saturating the remaining membrane attachment sites with heterologous nucleic acids to prevent the probe reagent from adhering to the membrane in a non-specific manner. All of these steps must be carried out before performing the actual hybridization.

Recent development of new technologies for synthesizing or depositing nucleic acids on substrates at very high densities have allowed the miniaturization of nucleic acid arrays yielding increased experimental efficiency and information content. (Lockhart & Winzeler, Genomics, Gene Expression and DNA Arrays, *Functional Genomics*, 405:6788, June 2000, 827-35). Utilizing these Biochips or Microarrays, one can conduct massively parallel experiments in genomics and proteomics with applications as diverse as, pharmacogenomics, gene expression, compound screening, toxicology, Single Nucleotide Polymorphism (SNPs) analysis, Short Tandem Repeats (STRs) and molecular diagnostics. It would be desirable to create a simple, cost-effective device that would produce a low background with optically clean fluorescent detection, allow oligonucleotides to be easily coupled in an array format, and be easily adapted to an automated manufacturing process.

SUMMARY OF THE INVENTION

The present invention is, in part, directed to a biochip, a platform which composes the biochip, and a stage which composes the platform. The platform comprises a stage.

The stage of the invention includes a carrier. The carrier has a first side which is hydrophilic and optically inactive. Disposed on the first side of the carrier is an aqueous matrix. The matrix is for attaching or embedding cross-linking agents, at least at the top surface of said matrix. The cross-linking agents attached to the top surface are for cross-linking sensing elements to the top surface of the matrix. The sensing elements are reactive to one or more analytes. Addition or attachment of cross-linking agents to at least the top surface of the stage matrix thereby forms the platform of the invention.

The platform is for building a biochip. The platform includes the stage. In other words, the platform has a carrier having a first side which is hydrophilic and optically inactive. An aqueous matrix is disposed on the first side for embedding cross-linking agents, at least at the top surface of said matrix. The cross-linking agents are for cross-linking sensing elements to the top surface of said matrix, the sensing elements being reactive to one or more analytes. The platform includes cross-linking agents attached to or embedded in the top surface of the matrix, and for cross-linking said sensing elements. Attachment of sensing elements to the cross-linking agent at least to the top surface of the platform thereby forms the biochip of the invention.

The biochip of the invention is for sensing analytes in a test or target sample. The biochip includes the platform of the invention. The platform includes the stage of the invention. Accordingly, the biochip of the invention includes a platform. The platform has a carrier having a first side which is hydrophilic and optically inactive. An aqueous matrix disposed on said first side for embedding cross-linking agents, at least at the top surface of said matrix. The cross-linking agents are for cross-linking sensing elements to the top surface of said matrix, said sensing elements being reactive to one or more analytes in a target or test sample. Included in the platform are cross-linking agents, attached to or embedded in at least the top surface of the matrix. Further included in the biochip are sensing elements cross-linked to the cross-linking agents in the top surface of said matrix.

Other objects, features, and advantages of the present invention will become more fully apparent from the following detailed description of preferred embodiments, the claims, and the accompanying drawings.

REFERENCE NUMERALS IN FIGS. 1-10 OF THE DRAWINGS

Figure 1:
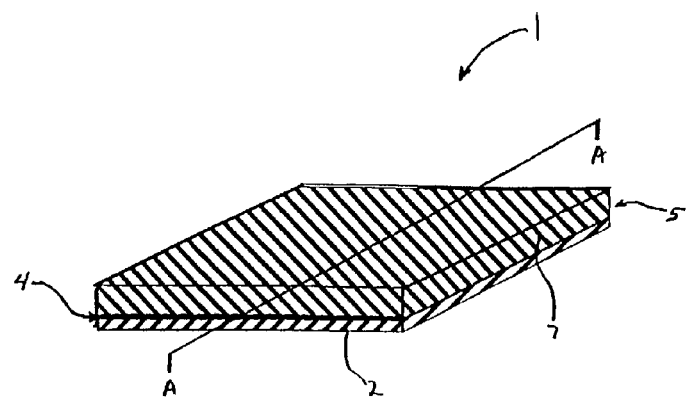
FIG. 1 is a perspective view of a stage comprising a single level matrix.

1 stage comprising a single level matrix
2 carrier
3 first side
4 hydrophilic bridging agent
5 matrix
6 top surface
7 light blocking agent (\\\\)
10 platform comprising a single level matrix
15 cross-linking agent
20 biochip comprising a single level matrix
25 nucleic acid sensing element
30 stage comprising a three level matrix
31 bottom level of matrix
32 middle level of matrix
33 top level of matrix
40 platform comprising a three level matrix
50 biochip comprising a three level matrix 65 marker
75 nucleic acid reporter probe
85 nucleic acid analyte of interest
A-A axis upon which cross-sectional views are taken

MODES OF CARRYING OUT THE INVENTION

General Description and Definitions

The practice of the present invention will employ, unless otherwise indicated, conventional biochemistry, molecular biology and recombinant DNA techniques within the skill of the art. Such techniques are explained fully in the literature. See, e.g. Maniatis et al., *Molecular Cloning: A Laboratory Manual* (1982); DNA Cloning: *A Practical Approach*, vol. I & II (D. Glover, ed.); *Oligonucleotide Synthesis*, (Gait, N., ed., 1984); *Nucleic Acid Hybridization*, B. Haines & S. Higgins, eds., (1985); Sambrook, J. et al. vol. 1-3, *Molecular Cloning, A Laboratory Manual*, 1989; Harwood, A. J., ed. (1996) *Basic DNA and RNA Protocols*, Humana Press, NJ; Glover, D. M. and Haines, B. D. (1995) *DNA Cloning: A Practical Approach*, $2^{nd}$ ed. vol. 1-4, IRL Press; Kriegler, M. (1990) *Gene Transfer and Expression, A Laboratory Manual*, Stockton Press, NY; *Molecular Biology and Biotechnology: A Comprehensive Desk Reference*, ed. Robert A. Meyers, VCH Publishers, Inc, (1995).

Further reference is made to standard techniques, materials, and equipment in biochips, and electronics for detecting, monitoring, and processing optical or electrical characteristic associated with the binding of analytes to sensing elements disposed on biochips. Factors, techniques, and equipment involved in biochip construction, performance and application of biochips to diagnostics, research, health care, control of industrial processes, environmental monitoring are explained fully in the literature. The electroanalytical methods of optico-analytical transducers and device construction are disclosed and explained in standard references ("*Microarray Biochip Technology*," Ed. Mark Schena, Eaton Publishing, Natick, Mass., 2000; literature available from Hamamatsu Corporation, Bridgewater, N.J.). Also available in the literature are methods for optimizing performance factors: selectivity, linear range, calibration, reproducibility, response time, lifetime and the factors affecting biochip performance (e.g. pH, buffers, methods and materials for immobilizing sensing elements. See, e.g., *Biosensors—An Introduction*, (1996), John Wiley & Sons Ltd.; Kress-Rogers, E., ed., *Handbook of Biosensors and Electronic Noses, Medicine, Food and the Environment* (1997), CRC Press; Bickerstaff, G. F. ed., (1997) *Immobilization of Enzymes and Cells*, Humana Press, Inc., Totowa, N.J.; *Bioconjugate Techniques*, Greg T. Hermanson, Academic Press, San Diego, Calif., (1996).

The following terminology will be used in accordance with the definitions set out below in describing the present invention.

Biochip

As used herein, the term "biochip" refers to a device of the present invention comprising sensing elements cross-linked to the top surface of the matrix of a platform (as defined below). The sensing elements possess a selective affinity for analytes of interest within a test sample. As described herein, a biochip of the invention includes a platform, the platform including a stage. For example, an embodiment of the biochip comprises a platform upon which is disposed an array of nucleic acid sensing elements used to examine gene activity or expression, identify gene mutations using a hybridization reaction between the sensing elements on the surface of the biochip and a target nucleic acid analyte. By way of example but not limitation, depending on the assay and needs of the user, sensing elements may be chosen to distinguish mutant from normal alleles, and/or to distinguishing gene expression products from mutant and normal alleles. Similarly, sensing elements may be chosen to distinguish gene expression in normal tissue from gene expression in diseased tissue.

Platform

As used herein, the term "platform" refers to a device of the present invention which composes or is a component of the biochip of the invention. The platform of the invention comprises a stage (as defined below) and cross-linking agents embedded at least at the top surface of the matrix of the stage. The cross-linking agents cross-link sensing elements to the top surface of the matrix, thereby forming a biochip.

Stage

As used herein, the term "stage" refers to a device of the present invention which composes or is a component of the platform of the invention. The stage of the invention comprises a carrier having a first side which has been rendered hydrophilic and optically inactive. Disposed over the first side is a matrix capable of embedding cross-linking agents at least at the top surface of the matrix, thereby forming a platform for building a biochip.

Sensing Element

The term "sensing element" refers to a macromolecule for detecting an analyte. The sensing element of the invention includes macromolecules preferentially selective or having a selective binding affinity for an analyte of interest. In assays and other protocols described herein which employ luminometric/fluorometric/colorimetric and/or radioactive markers and/or reporters, the reaction between sensing element and analyte of interest generates a detectable optical event which results in a signal that can be monitored by an optical reader. Sensing elements include, but are not restricted to:

1 Synthetic or biologically produced nucleic acid (i.e. target specific capture probe or ligand binder probe) which by design contain specific, complimentary nucleotide sequences that allow the capture probe to hybridize or bind to an analyte of interest, for example a target nucleic acid sequence. The capture probe may be deoxyribonucleic acid (DNA), ribonucleic acid (RNA), oligonucleotides, polymerase chain reaction products, or a combination of these nucleotides (chimera), which may be synthesized chemically, isolated from a biological source, or cloned. A nucleic acid sensing element, i.e. target capture probe, may be a linear strand or may contain branch points to increase the density of immobilized probe. The capture probe may provide single or multiple copies of the sequence complimentary to the target nucleic acid. The capture probe is selected to specifically hybridize or bind a target nucleic acid. When more than one capture probe is used in a hybridization assay, each probe should recognize a unique sequence or ligand separated apart from other target sequence(s) or ligands with the target molecules.

2. Proteins. As used herein, a "target specific capture probe" also refers to synthetic or biologically produced ligand-binding amino acid sequences that allow the protein capture probe to recognize and bind to a target analyte. Protein capture probes, which include enzymes, may be naturally occurring or synthetic, and employed in their unaltered or isolated state or as aggregates with other species. Examples of receptors functioning as capture probes which can be employed by this invention, include, but are not restricted to, antibodies, cell membrane receptors, antibodies (monoclonal or polyclonal), and anti-sera reactive with specific antigenic determinants (such as on viruses, cells, or other materials), drugs, peptides, co-factors, lectins, polysaccharides, cells, cellular membranes, and organelles. Other examples of receptors which can be investigated by this invention include but are not restricted to:

a. microorganism receptors
b. enzymes
c. antibodies
d. catalytic polypeptides
e. hormone receptors
f. opiate receptors Cross linking systems for attaching sensing elements that are proteinacious to the top surface of the matrix of the biochip are well known in the art (*Bioconjugate Techniques*, Greg T. Hermanson, Academic Press, San Diego, Calif., (1996).

It should be understood that any macromolecule capable of specifically recognizing and binding to an analyte may be a sensing element of the invention. Such macromolecules (also known in the art as bioaffinity agents) rely on molecular recognition of an analyte as the first step in the generation of a response by a biochip. Strategies for selecting the appropriate bioaffinity agent for an analyte of interest are well known in the art (See Chapter 3 in Kress-Rogers, E. 1997, *Handbook of Biosensors and Electronic Noses: Medicine, Food, and the Environment*, [ed., Kress-Rogers, E.], CRC Press, Boca Raton). A sensing element is further defined to be any macromolecule that when activated by the binding of a chemical ligand or specific analyte, in combination with the addition of appropriate optical labels, causes generation of a detectable optical signal, and operates to communicate the presence of said ligand or analyte from the sample comprising analytes or ligands for detection through an optical reader. The sensing elements of the invention are capable of detecting thousands of natural and synthetic molecular species (analytes). In principal, the range of chemical structures that can be detected by sensing elements in the device and methods of the invention is unlimited (Kress-Rogers, E. 1997, *Handbook of Biosensors and Electronic Noses: —Medicine, Food, and the Environment*, [ed., Kress-Rogers, E.], CRC Press, Boca Raton). According to the conditions of the detection method, the binding of the analyte to the sensing element yields a colorimetric event (e.g. absorption of incident light, fluorescence, phosphorescence, luminescence) that is, a signal, which, when processed or monitored by an optical reader indicates the presence or concentration of an analyte of interest in the target sample.

The term sensing element is used herein to include a plurality or array of different macromolecules respectively specific for a plurality of specific analytes; or a plurality or array of different macromolecules specific for a single analyte.

Scope of Analytes Detectable by Device and Method of the Invention

It should be understood that the scope of analytes in aqueous solutions of interest which can be detected by the sensing elements in the device and methods of the invention is extremely large. Known sensing elements respond to a vast number and variety of analytes, which include but are not limited to those enumerated in Beer, H. In, *Handbook of Biosensors and Electronic Noses: Medicine, Food and the Environment* (1997) CRC Press, pp. 521-532; Alone, E., In, *Handbook of Biosensors and Electronic Noses: Medicine, Food and the Environment* (1997) CRC Press, pp. 503-519. Nevertheless, they are readily detected and discriminated. The inherent molecular specificity in recognizing and discriminating myriads of foreign compounds should be understood to be a characteristic of sensing element macromolecules, which, using manufacturing techniques well known in the art described above, are design-engineered as sensing elements disposed on the devices of the invention.

Analyte or Ligand

As used herein, the terms analyte and ligand are used interchangeably. A ligand is a molecule that is recognized by a particular sensing element. The agent bound by or reacting with a sensing element is called a "ligand," a term which is, by definition, meaningful only in terms of its counterpart sensing element. The term "ligand" does not imply any particular molecular size or other structural or compositional feature other than that the substance in question is capable of binding or otherwise interacting with the sensing element. The ligand may serve either as the natural ligand to which the sensing element binds, or as a functional analogue. Examples of ligands that can be investigated by this invention include, but are not restricted to, oligonucleotides, nucleotides, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, oligosaccharides, proteins, and antibodies (monoclonal and/or polyclonal).

Hybridization

As used herein, "hybridization" is the process by which two partially or completely complementary strands of nucleic acid are allowed to come together, under predetermined reaction conditions, in an antiparallel fashion to form a double stranded nucleic acid with specific and stable hydrogen bonds. The nucleic acid capture probe sequence is selected to specifically interact with the target molecule or analyte at a pre-determined degree of stringency. The probe length is pre-determined to provide the required specificity at the degree of stringency used in the assay. Assay conditions are set so that the stringency of hybridization between the capture probe and the target nucleic acid provides the required specificity.

Target/Test Samples

As used herein, "target samples" or "test samples" refer to aqueous aliquots which comprise one or more analytes of interest for detection when brought into contact with the sensing elements. Target samples include without restriction, biological or non-biological samples. Biological samples include, but are not restricted to fluids, cells, subcellular components, and all other biological matter derived from animals, plants, microorganisms, and viruses. Non-biological samples refer to liquid and gaseous environmental samples, which may also include biological matter; and to samples derived from process stream monitoring in the food and non-food industries.

Optical Inactivity or Optically Inactive

As used herein, "optically inactive" means a material or surface thereof which produces low reflectivity, low fluorescence, and low scatter properties for optimal optical detection of the target molecules in the present invention. A carrier having a side which is optically inactive, according to this invention, has been otherwise rendered so that optical activity emitted from or through the surface of the carrier is substantially or completely quenched.

The carrier of the invention may be rendered optically inactive such as by disposing one or more light blocking agents directly to the surface of the carrier or mixed with the matrix disposed on the carrier. Alternatively, the carrier may inherently possess optically inactive properties, such that rendering by light blocking agents is not necessary.

Colorimetric Event/Fluorescence

In colorimetric-event detection, and in particular fluorescence-detection methods, a fluorescent molecule has the ability to absorb photons of energy at one wavelength and subsequently emit the energy at another wavelength. Fluorescence is caused by incident radiation impinging upon or exciting an electron of a molecule. The electron absorbs the incident radiation and is raised from a lower quantum energy level to a higher one. The excess energy is released as photons of light as the electrons return to the lower, ground-state energy level. See "*Bioconjugate Techniques*," Greg T. Hermanson, Academic Press, San Diego, Calif., (1996), and "*Principles of Biochemistry*," Lehninger, et al., $2^{nd}$ ed., 1993, for a detailed description of fluorescent labeling and detection techniques.

Devices and methods for detecting or reading fluorescence caused by the capture of an analyte(s) of interest by a sensing element mounted on the carrier of the invention are well known in the art ("*Microarray Biochip Technology*," Ed. Mark Schena, Eaton Publishing, Natick, Mass., 2000; "*Bioconjugate Techniques*," Greg T. Hermanson, Academic Press, San Diego, Calif., (1996); "*Principles of Biochemistry*," Lehninger, et al., $2^{nd}$ ed., 1993, for a detailed description of fluorescent labeling and detection techniques.) References on fluorescent tags, labels, or markers include Lakowicz, J. R. (ed.) (1991) "Topics in Fluorescence Spectroscopy," vols. 1-3. Plenum, New York; Bright, F. V. (1988) Bioanalytical applications for fluorescence spectroscopy. *Anal. Chem.* 60, 1031A; Dewey, T. G. (ed.) (1991) "Biophysical and Biochemical Aspects of Fluorescence Spectroscopy." Plenum, New York; McGown, L. B., and Warner, I. M. (1990) Molecular fluorescence, phosphorescence, and chemiluminescence spectroscopy. *Anal. Chem.* 190, 2558; Ploem, J. S., and Tanke, H. J. (1987) "Introduction to Fluorescence Microscopy." Oxford Univ. Press, London; Darzynkiewicz, Z., and Chrissman, H. A. (eds.) (1990) Flow cytometry. *Methods Cell Biol.*; Haughland, R. P. (1991) Fluorescent labels. in "Biosensors with Fiberoptics" (D. L. Wise and L. B. Wingard, eds.), pp. 85-109. Humana Press, Totowa, N.J.; and Waggoner, A. S. (1990) Fluorescent probes for cytometry. in "Flow Cytometry and Sorting" (M. R. Melamed, T. Lindmo, and M. L. Mendelsohn, eds.), $2^{nd}$ ed., pp. 209-225. Wiley-Liss, New York.

Further especially contemplated optical detection methods include detection of luminescence and detection of absorption of a portion or particular wavelength of light within the UV/VIS spectrum. There are numerous methods and configurations for detection of luminescence and absorption known in the art, and all known methods are considered suitable for use in conjunction with the teachings presented herein.

Markers/Reporter Probes

As used herein, a "marker" is any agent that can be used to label proteins, nucleic acids, and other molecules as disclosed in the context of the present invention. One of skill in the art selects appropriate markers required to suit the detection method used and needs of the assay. A "reporter probe" refers to a labeled molecule that yields a colorimetric event upon exposure to excitation energies. The reporter probes of the present invention possess a selective affinity (i.e., a tendency to react or combine with atoms or compounds of different chemical constitution (See Hawley's Condensed Chemical Dictionary, $13^{th}$ ed., Richard L. Lewis (rev.), International Thomson Publishing, Inc., NY, 1997)) for the analytes of interest within the test sample.

It should be understood that the terms "marker" and "reporter probe" in context may be used interchangeably. Since each marker has its own colorimetric character, more than one labeled molecule, each tagged with a different marker, can be used at the same time to detect two or more analytes of interest. Markers known in the art that are useful for the present invention include, but are not limited to, Cyanine 3 (Cy3), Cyanine 5 (Cy5), and those enumerated in "*Microarray Biochip Technology*," Mark Schena (ed.), Eaton Publishing, Natick, Mass., 2000; "*Bioconjugate Techniques*," Greg T. Hermanson, Academic Press, San Diego, Calif., (1996); "*Principles of Biochemistry*," Lehninger, et al., $2^{nd}$ ed., 1993; "*Antigen Retrieval Techniques: Immunohistochemistry and Molecular Morphology*," Shan-Rong Shi, Jiang Gu, Clive R. Taylor (eds.), Eaton Publishing, Natick, Mass., 2000; "*Immunological Reagents & Solutions: A Laboratory Handbook*" Bassam B. Damaj, Eaton Publishing, Natick, Mass., 2000; "*Protein Staining and Identification Techniques*," Robert C. Allen, and Bruce Budowle, Eaton Publishing, Natick, Mass., 1999; "*Affinity and Immunoaffinity Purification Techniques*," Terry M. Phillips, and Benjamin F. Dickens, Eaton Publishing, Natick, Mass., 2000.

Light Blocking Agents/Signal-to-Noise Ratio

As used herein, "light blocking agents" refer to agents or treatments that render a surface optically inactive thereby mitigating, preventing, minimizing, reducing background fluorescence emanating from the carrier, which thereby optimizes the signal to noise ratio for the detection method, e.g. fluorescence detection. Particularly preferred light blocking agents include metal oxides (e.g., iron oxide), organic compounds (e.g., graphite, dyes, etc.), and all reasonable combinations thereof.

"Signal-to-noise ratio" quantifies how well one can resolve a true signal from the noise of the system. It is typically computed by dividing a specific signal by the back ground/noise signal. If a microarray detecting system has a poor signal to noise ratio, the variation in the signal alone can prevent accurate quantitation of each spot ("*Microarray Biochip Technology*," Mark Schena (ed.), Eaton Publishing, Natick, Mass., 2000).

Reader/Detector

As used herein, a "reader or detector" refers to any device used to measure the signal generated by the binding of analytes of interest to the sensing elements. Readers or detectors of optical signals, including fluorescence, are well known in the art and adapted for reading biochips ("*Microarray Biochip Technology*," Mark Schena (ed.), Eaton Publishing, Natick, Mass., 2000).

Carrier

A variety of materials and formats, depending on the needs of the user, are suitable for forming the carrier. The carrier may be formed of a material that is rigid or flexible, and may be reflective or transmissive. A wide range of rigid materials may be used to form the carrier, including one or more of glass, silicon, fused silica, plastic, ceramic, metal, semiconductor materials, and combinations thereof. The carrier may be of any thickness desired. Flexible carriers include, but are not restricted to thin sheets of polyester, polystyrene, polyethylene, paper, woven and non-woven textile and like materials.

Matrix

As used herein, the term "matrix" refers to a medium wherein something is formed, develops, embedded, attached or enclosed. The matrix of the invention is preferably a meshwork of solubilized or suspended agents. The meshwork of solubilizable agents is largely polysaccharide in nature. It should be understood that the matrix coating may be any agent that protects the integrity of the cross-linking agents. The matrix is capable of embedding the cross-linking agents, which cross-links the sensing elements to the surface of the matrix. Materials useful as matrix coatings include, but are not limited to gelatin, polyvinyl alcohol, polyvinyl pyrrolidone, agarose, polyacrylamide and blends of the above.

Cross-Linking Agents

A cross-link is a covalent bond between two macromolecular moieties, usually formed when two macromolecular free radicals combine. Chemical modifications or conjugation processes to achieve cross-links involve the reaction of one functional group with another, resulting in the formation of a covalent bond. The creation of bioconjugate reagents with reactive or selectively reactive functional groups forms the basis for simple and reproducible cross-linking or tagging of target molecules ("*Bioconjugate Techniques*," Greg T. Hermanson, Academic Press, San Diego, Calif., (1996)).

As used herein, "cross-linking agents" include, but are not limited to homobifunctional linkers, heterobifunctional linkers, and zero-length cross-linkers. Homobifunctional linkers are linkers with two reactive sites of the same functionality, such as glutaraldehyde. These reagents could tie one protein to another by covalently reacting with the same common groups on both molecules. Heterobifunctional conjugation reagents contain two different reactive groups that can couple to two different functional targets on proteins and other macromolecules. For example, one part of a cross-linker may contain an amine-reactive group, while another portion may consist of a sulfhydryl-reactive group. The result is the ability to direct the cross-linking reaction to selected parts of target molecules, thus garnering better control over the conjugation process. Zero-length cross-linkers mediate the conjugation of two molecules by forming a bond containing no additional atoms. Thus, one atom of a molecule is covalently attached to an atom of a second molecule with no intervening linker or spacer. One of ordinary skill in the art would refer to "*Bioconjugate Techniques*," Greg T. Hermanson, Academic Press, San Diego, Calif., (1996), for a detailed description of cross-linking agents.

In the present invention, cross-linking agents are physically suspended on or in supporting material (matrix) which serves to immobilize or attach or embed the sensing elements held within and at the top surface of the matrix.

A preferred cross-linking agent involves avidin. Without limitation, avidin can be strepavidin, modifications, thereof, or avidin. Avidin can be coupled with agarose by various chemistries. Ideally, strepavidin is embedded in the surface layer of the matrix coating, binding essentially irreversibly to biotinylated sensing elements (e.g. sensing elements which are nucleic acids). See "*Bioconjugate Techniques*," Greg T. Hermanson, Academic Press, San Diego, Calif., (1996). Strepavidin (or any protein containing a lysine) will react with the aldehyde of NUFIX™ (glyoxyl agarose), a commercially available aldehyde-activate matrix. Cross-linking system for linking a proteinacious capture probe to the platform of the invention are well known, ibid.

Further especially contemplated cross-linking agents include those in which the cross-linking agent forms a non-covalent bond by at least one of a metal-chelate interaction (e.g., $Ca^{2+}$ chelated by polyaspartate, boron compounds chelated by polyalcohols, or nickel compounds chelated by histidine, etc.), a hydrophobic interaction (e.g., via a leucine zipper), hydrogen bonding (e.g., between amine and keto group), a polar/non-polar interaction (e.g., acid/basic amino acid interaction), and electrostatic interaction (e.g., between $NH_3^+$ and $CO_2^-$).

Stage for Building a Platform

Figure 2:
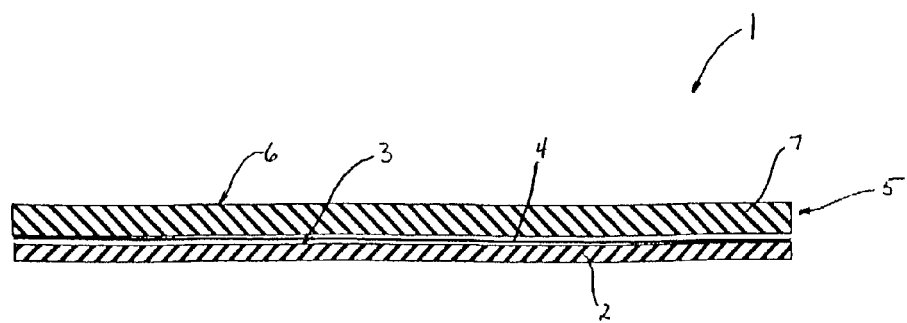
FIG. 2 is a cross-sectional view of a stage at A-A comprising a single level matrix.
Figure 5:
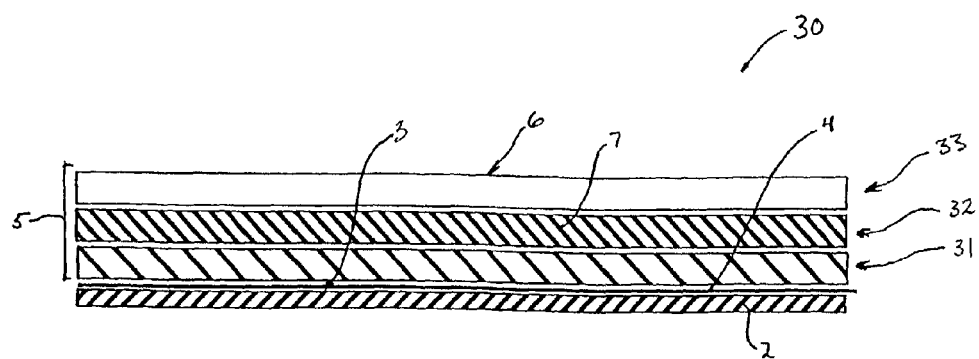
FIG. 5 is a cross-sectional view of a stage at A-A comprising a three level matrix.

Referring to FIGS. 1, 2, and 5, in one aspect, the invention involves a stage (1, 30) for building or fabricating a platform (10, 40). The platform, as described in detail below, is useful as a component for forming the biochip (20, 50) of the invention. The stage (1) has a carrier (2) which has a first side (3). In one embodiment, the first side (3) has been rendered hydrophilic by a hydrophilic bridging agent (4), and optically inactive by a light blocking agent (7).

As described in detail below, an embodiment of the stage (1) involves a single-level matrix (5), disposed on the first side (3) of the carrier (2). In preferred embodiments of the stage (30), the matrix (5) involves two or more levels (31, 32, 33) (FIG. 5). In any case, except in which the carrier (2) is inherently optically inactive, any level of the matrix (5) may contain a light blocking agent (7) to control elevation of the background signal. One of skill in the art will select the appropriate concentration of light blocking agent (7) required to control the signal-to-noise ratio to suit the detection method used and needs of the assay.

Addition of a cross-linking system, i.e. cross-linking agents (15), to at least the top surface (6) of the matrix (5) thereby forms a platform (10, 40). The cross-linking agents (15), which are attached or embedded to the top surface (6) of the platform (10, 40), cross-link sensing elements (25) to the top surface (6) of the matrix (5), thereby forming a biochip (20, 50) from the platform (10, 40). One of skill in the art will select the appropriate cross-linking agents (15) and amounts thereof required to cross-link sensing elements (25) to the top surface (6) of the matrix (5) to suit the detection method used and needs of the assay.

The carrier (2) may be formed in various formats from a variety of materials depending on the needs of the user. The carrier (2) may be formed of a material that is rigid or flexible, and which, depending on the embodiment, may be optically active or optically inactive. A wide range of rigid materials may form the carrier, including glass, silicon, fused silica, plastic, ceramic, metal, and semiconductor materials. The carrier may be of any thickness desired to suit the detection method used and needs of the assay. Flexible carriers include, but are not restricted to thin sheets of polyester, polystyrene, polyethylene, paper, woven and non-woven textile and like materials.

Carrier formats may be formed by cutting, sawing, scribing, laser scribing, shearing, or otherwise forming the carrier into the desired size or shape depending on the reaction conditions, detection method, and detection system used. The carrier can be formed into a broad range of geometric planar configurations circumscribed as polygonal, circular, and free form. A typical geometric shape would be a circle or square (FIG. 1). For example, one suitable geometric configuration of the carrier for a single use assay is a rectangle, 0.50 inch×1.0 inch. Another example is a square, 0.50 inch by 0.50 inch. Carrier sizes are not restricted to the above, as alternative formats and assays may require substantially more or less reactive test surface.

The material selected for the carrier (2) may either be inherently hydrophilic or may require rendering such that the surface of the first side (3) is rendered hydrophilic. Hydrophilicity is defined as having a strong tendency to bind or absorb water, which results in swelling and formation of reversible gels (*Hawley's Condensed Chemical Dictionary*, 13$^{th}$ ed., Richard L. Lewis (rev.), International Thomson Publishing, Inc., NY, 1997). It is desirable to render the first side (3) or the surface of the first side of the carrier (2) hydrophilic to allow adhesion of an aqueous matrix (5) coating to the carrier (2). Various methods are known in the art to render surfaces hydrophilic. In an embodiment of the invention, a hydrophilic bridging agent (4) is applied to the surface of the first side (3) of carrier (2). A typical hydrophilic bridging agent is gelatin. Alternatively, the carrier may undergo Corona Ion treatment, in which the surface is ionized with a charge that is stronger than the hydrophobic properties of the carrier. Various carrier materials may be purchased precoated with gelatin from the Dupont Corporation. One of ordinary skill in the art would refer to Markgraf, D. A., "Corona Treatment: An Overview," 1986 Coextrusion Conference Proceedings, TAPPI PRESS, Atlanta, p. 85; Marra, J. V., "Surface Modification of Polypropylene Film." 1985 Polymers, Laminations and Coatings Conference Proceedings, TAPPI PRESS, Atlanta, p. 103; Thompson, K., "Surface Treatments for Coex Polymer Films/Coatings," 1989 Coextrusion Conference Proceedings, TAPPI PRESS, Atlanta, p. 11; literature available from Enercon Industries Corporation, Germantown Wis., for principles, methods, and materials for preparing hydrophilic surfaces.

An aqueous matrix (5) is disposed on the hydrophilic first side (3) of the carrier (2). A matrix is a medium wherein something may be formed, developed, or embedded. The matrix (5) of the invention is preferably a meshwork of solubilized or suspended agents. The meshwork of solubilizable agents is largely polysaccharide in nature. Materials useful as matrix coatings include, but are not limited to gelatin, agarose, polyacrylamide and blends of the above. A preferred matrix material is agarose. One of skill in the art will select the appropriate matrix material required to suit the detection method used and needs of the assay. Depending on the material selected for the matrix, it may be desirable to add one or more reagents to achieve chemical stability and/or optimal pH for the desired assay.

Preferably, surfactants are added to the matrix (5) to enhance the aqueous properties of the matrix to optimize coating of the carrier (2). A surfactant is any compound that reduces interfacial tension between a liquid and a solid (*Hawley's Condensed Chemical Dictionary*, 13$^{th}$ ed., Richard L. Lewis (rev.), International Thomson Publishing, Inc., NY, 1997). Surfactants useful in the invention may be ionic, non-ionic, zwitterioninc, or amphoteric. Preferably, the surfactants include, but are not limited to commercially available TWEEN (polyoxyethylenesorbitan monostearate), BRIJ (polyoxyethylene ether), TRITON (polyoxyethylene), sulphonates and the salts thereof, quaternary ammonium compounds, thoxylates, amides, and fatty acids.

Preferably, buffers are added to stabilize the pH of the matrix coating for optimal hybridization conditions. See "*Principles of Biochemistry*," second edition, Lehninger, Nelson, and Cox, for details regarding hybridization reaction conditions. Commercially available buffers include, but are not limited to methane-ethane sulphonic acid, phosphate, Tris, and Hepes.

In an embodiment, the matrix (5) comprises one or more humectants to reduce or control the shrinking and swelling of the matrix. A humectant is a substance having an affinity for water with stabilizing action on the water content of a material (*Hawley's Condensed Chemical Dictionary*, 13$^{th}$ ed., Richard L. Lewis (rev.), International Thomson Publishing, Inc., NY, 1997). It may be desirable to control surface irregularities (e.g. elevations and/or depressions) of the matrix for accurate detection optical signals by a reader. Otherwise, a technician would have to constantly recalibrate the reader to compensate for minute irregularities in the matrix caused by shrinking and swelling of the matrix from the addition of capture probes, i.e. sensing elements (25), aqueous test samples containing target molecules (85), and reporters (75). Albeit a planar surface without irregularities may not be achieved, nonetheless, humectants are useful for minimizing surface irregularities. Suitable humectants include, but are not limited to glycerin, oils, sugars, and some detergents.

In those embodiments of the platform (10, 40) in which the carrier (2) inherently provides stray, background, or otherwise undesirable optical signals, the carrier may be rendered optically inactive such as by application of one or more light blocking agents (7) directly to the first side (3) of the carrier (2) or mixed with the matrix (5) disposed on the carrier. Alternatively, if the material selected for the carrier inherently possesses optically inactive properties, rendering by light blocking agents is optional.

For optically-based detection methods, it is desirable to optimize signal-to-noise ratio. For example, in fluorescence-based assays, it is desirable to add one or more light blocking agents (7) to the matrix (5) coating. In those embodiments of the invention where it is desirable to use polyester as the carrier, optically pure polyester is preferred as impurities found in polyester may fluoresce and cause undesirable background signal or noise. The addition of a light blocking agent (7) to the matrix (5) serves to prevent or minimize these inherent fluorescent qualities from disrupting the detection or reading of the optical signal generated from or as a consequence of the binding of analyte(s) of interest (85) to one or more sensing elements (25). Agents useful as light blocking agents include, but are not limited to iron oxide, titanium dioxide, carbon black, and mixtures of the above. In a preferred embodiment of the stage (30), the matrix includes a sufficient amount of iron oxide to render the carrier (2) optically inactive.

In a more preferred embodiment of the stage (3), the carrier (2) is formed from hydrophobic, optically pure Mylar, 100 microns in thickness. Mylar emits a significant amount of background, stray, or otherwise undesirable optical signal, e.g. fluorescence. Such material is commercially available from the Dupont Corporation and is used widely in the photographic film coating industry. The carrier is provided with a gelatin coating on the first side (3), which acts as a hydrophilic bridging agent (4) to allow attachment of the aqueous matrix (5) coating. In a version of this embodiment, the matrix has three levels (31, 32, 33 in FIGS. 5, 6, 7). The bottom level (31) of the matrix (5) is disposed on the gelatin (4), and is a standard agarose in water solution ranging from about 1% to about 5%, with 1% being preferable. The bottom level (31) contains the surfactant TWEEN-20 (polyoxyethylenesorbitan monostearate) and is buffered by HEPES. The bottom level (31) is applied at 200 ml of liquid matrix to 1 m$^2$ of carrier (2) material, which ultimately yields a wet thickness of 200 microns (dry thickness is approximately 10% of the wet thickness). The middle level (32) is a standard agarose in water solution ranging from about 1% to about 5%, with 1% being preferable. The middle level (32) contains a 3% dispersion of the light blocking agent (7) iron oxide, the surfactant TWEEN-20 (polyoxyethylenesorbitan monostearate) and is buffered with methane ethane sulphonic acid (MES). Like the bottom level (31), the middle level (32) is applied at 200 ml of solution to 1 m$^2$ of carrier (2), which yields a wet thickness of 200 microns. The middle level (32) serves to block the incident light from penetrating the matrix (5) and contacting the carrier (2), and prevents any optically active impurities within the carrier from causing undesirable background signal or noise, thereby rendering the carrier optically inactive. The top level (33) is an aldehyde-activated agarose in water solution ranging from about 1% to about 5%, with 1% being preferable.

Platform for Building a Biochip

Figure 3:
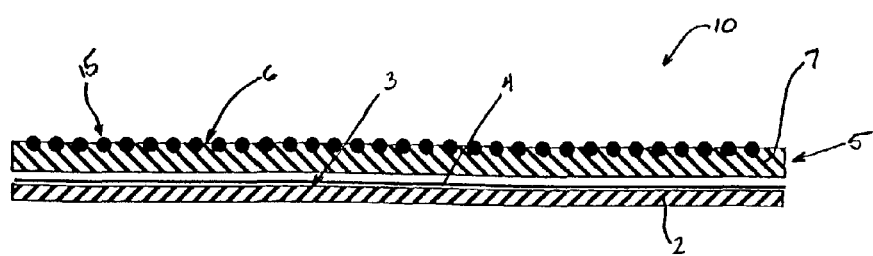
FIG. 3 is a cross-sectional view of a platform comprising a single level matrix.
Figure 6:
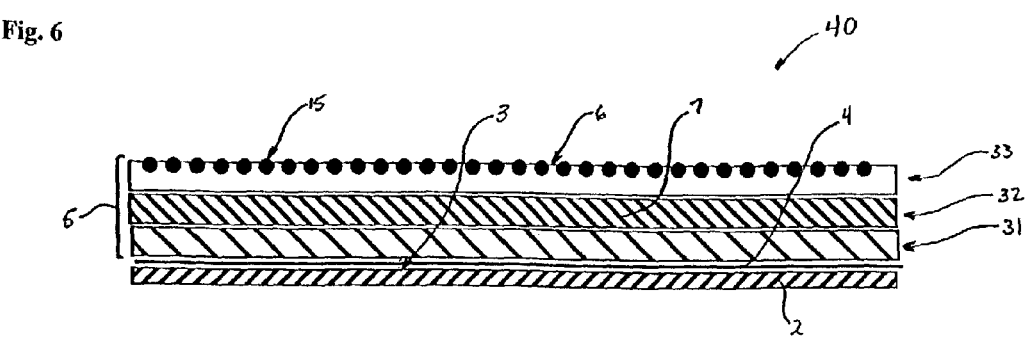
FIG. 6 is a cross-sectional view of a platform comprising a three level matrix.

Referring to FIGS. 3 and 6, another aspect of the invention is directed to a platform (10, 40) for building a biochip (20, 50). The platform comprises the stage (1, 30 of FIGS. 2 and 5) and cross-linking agents (15) attached to or embedded at least at the top surface (6) of the matrix (5) of the stage. The cross-linking agents (15) cross-link sensing elements (25) to the top surface (6) of the matrix (5), thereby forming a biochip.

The platform (10, 40) is formed by adding a sufficient amount of appropriate cross-linking agents (15) at least to the top surface (6) of the stage. The cross-linking agents (15) allow one or more sensing elements (25), as described below, to attach or cross-link to the top surface (6) of the matrix (5). The sensing elements (25) possess a selective affinity for one or more analytes of interest (85).

As described above, cross-linking agents (15) useful in the invention include, but are not limited to homobifunctional linkers, heterobifunctional linkers, and zero-length cross-linkers. Cross-linking agents (15) are physically suspended on or in the matrix (5) which serve to immobilize the sensing elements (25) held within and at the top surface (6) of the matrix. A preferred cross-linking system is the heterobifunctional group consisting of biotinstrepavidin, i.e. biotinylated sensing elements bound to avidin-coupled agarose. Ideally, strepavidin is embedded within and on the surface of the matrix, binding essentially irreversibly to the biotinylated sensing elements. Such cross-linking agents are commercially available from the Pierce Company and the Aldrich Company.

In a preferred embodiment of the platform (10, 40), the top level (33) of the matrix (5) coated during stage fabrication further includes streptavidin (a bifunctional cross-linker), attached to the top surface (6) of the matrix, dibasic sodium phosphate buffer and a surfactant. The top level (33) involves an aldehyde-activated agarose, commercially available as NUFIX™ (glyoxyl agarose), which reacts with the primary epsilon amine of the lysine group of strepavidin to form a Schiffs Base. This unstable bond is then reduced, with the addition of sodium cyanoborohydride, to yield a stable covalent bond with strepavidin. The unreacted aldehyde in the top level (33) of the matrix (5) is then quenched with histidine.

Biochip

Figure 4:
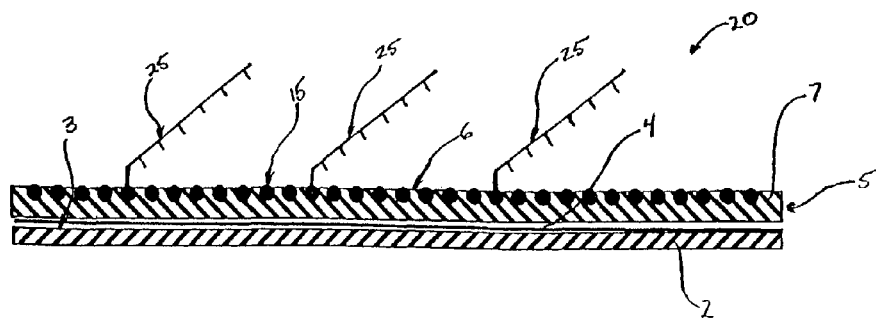
FIG. 4 is a cross-sectional view of a biochip comprising a single level matrix, showing nucleic acid sensing elements cross-linked to the platform of FIG. 3.
Figure 7:
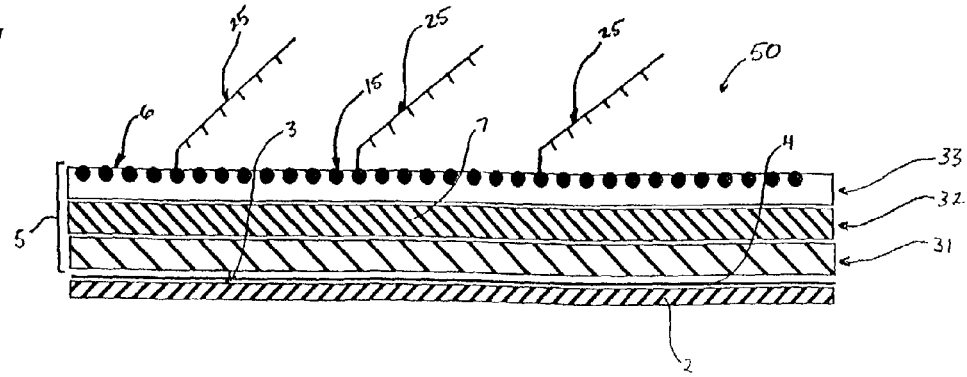
FIG. 7 is a cross-sectional view of a biochip comprising a three level matrix, showing nucleic acid sensing elements cross-linked to the platform of FIG. 6.
Figure 8:
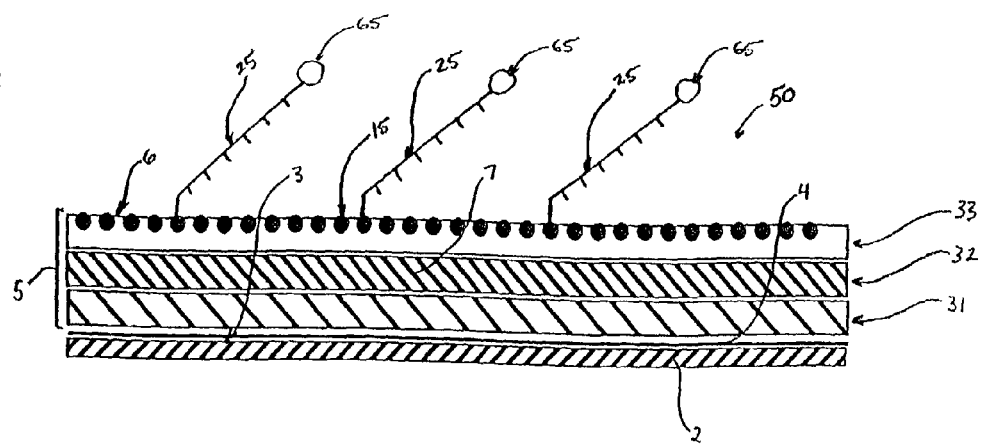
FIG. 8 is a cross-sectional view of a biochip comprising a three level matrix, showing fluorescent markers attached to the nucleic acid sensing elements.
Figure 9:
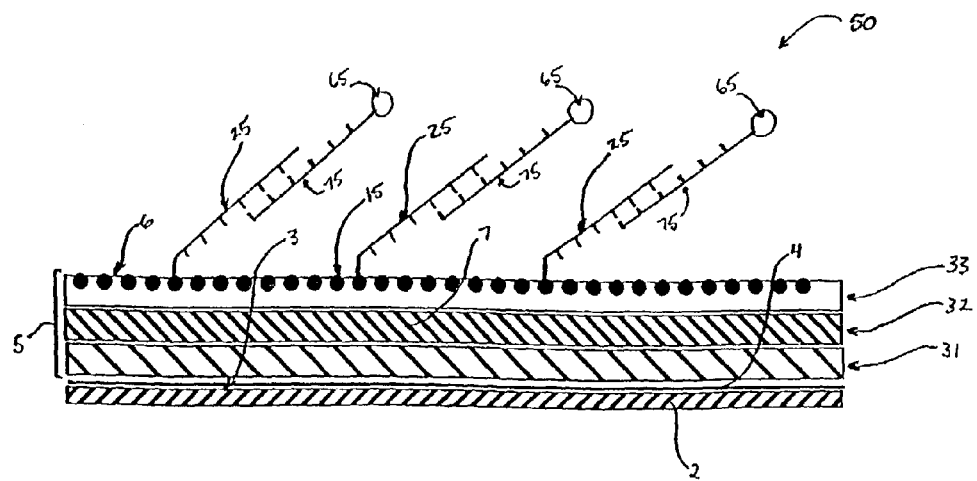
FIG. 9 is a cross-sectional view of a biochip comprising a three level matrix, showing nucleic acid reporter probes hybridized to the nucleic acid sensing elements.
Figure 10:
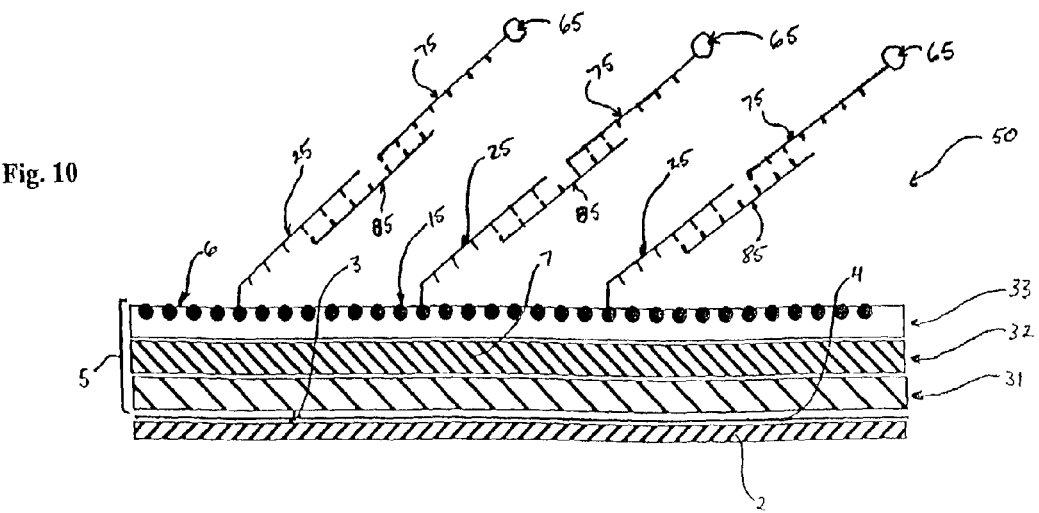
FIG. 10 is a cross-sectional view of a biochip comprising a three level matrix, showing nucleic acid reporter probes hybridized to the nucleic acid analytes of interest, which are hybridized to the nucleic acid sensing elements.

Referring to FIGS. 4 and 7, another aspect of the invention is directed to a biochip (20, 50). The biochip comprises the platform (10, 40) and sensing elements (25) cross-linked to the cross-linking agents (15) attached to or embedded in the top surface (6) of the matrix (5) of the platform.

Sensing Elements

Sensing elements (25) useful in the invention include macromolecules preferentially selective for an analyte of interest (85). Sensing elements (25) include, but are, not restricted to synthetic or biologically produced nucleic acid and synthetic or biologically produced ligand-binding amino acid sequences. It should be understood that the sensing elements (25) selected should possess at least one functional group adapted to covalently bond with an available functional group of the cross-linker attached to the top surface (6) of the matrix (5), thereby achieving adhesion of the sensing element (25) to the top surface of the matrix. Methods for forming sensing elements possessing at least one functional group, as described in this paragraph, are disclosed herein.

In a preferred embodiment of the invention, the sensing elements (25) are biotinylated (i.e., bound to biotin) and are deposited or brought into contact with cross-linking agents (25) (e.g. strepavidin) attached or embedded to the top surface (6) of the matrix (5) of the platform (10, 40). Strepavidin and biotin are an example of across-linking system. The biotin binds essentially irreversibly to the strepavidin at the top surface (6) of the matrix (5). Biotinylated sensing elements are commercially available from many sources (e.g. Aldrich, Pierce, Sigma).

Depositing Sensing Elements onto the Top Surface of the Platform

Commonly used techniques in the art are available for depositing sensing elements (25) onto the top surface (6) of the matrix (5) of the platform (10, 40). The sensing elements (25) are typically deposited in droplets with a spot diameter ranging from about 20 to 1000 µm, preferably 120 µm spaced about 200 µm apart. The platform (10, 40) is suitable for spotting by all contact and non-contact methods. Spotting devices and techniques known in the art include, but are not limited to, syringe-solenoid, solid pin replicator, quill and split pin, tweezer, PIN-AND-RING™, and jetting and piezo-electric pumps. One of ordinary skill in the art would refer to "Microarray Biochip Technology," Ed. Mark Schena, Eaton Publishing, Natick, Mass., 2000, for a detailed description of spotting techniques.

Reporter Probes

Reporter probes (75) useful in the invention include labeled macromolecules or other analytes which possess a selective affinity, i.e., are preferentially selective, for a sensing element, or, in another embodiment, for an analyte of interest (85), which has bound to the sensing element (25) on the top surface (6) of the matrix (5). Reporter probes (75) include, but are not restricted to synthetic or biologically produced nucleic acid sequences and synthetic or biologically produced ligand-binding amino acids sequences. The reporter probe (75) selected should possess a selective affinity for the analytes of interest (85), bound to the sensing element (25) on the top surface (6) of the matrix (5), thereby achieving adhesion of the marker probe to the analyte of interest.

In a preferred embodiment of the invention, the reporter probes (75) contain either the Cy3 or Cy5 marker (65) and are deposited onto the top surface (6) of the matrix (5) following adhesion of the analyte of interest (85) to the sensing element (25). The reporter probe (75) will react, combine, or otherwise bind to an analyte (85) of interest, thereby causing a colorimetric effect upon exposure to excitation energy. This colorimetric effect indicates the presence of the analyte of interest (85). Reporter probes that are design-engineered specifically to the user's requirements are commercially available from NEN Life Science Products, Boston, Mass.

While the above description provides exemplary configurations of contemplated biochips, it should be appreciated that various modifications may be made without departing from the inventive concept presented herein. For example, additional matrix layers with same or different functions may be added, or the substrate may already include a hydrophilic surface as discussed above.

Consequently, in further particularly preferred aspects of the inventive subject matter contemplated biochips may have a carrier with a hydrophilic surface. The term "hydrophilic"

as used herein refers to a physico-chemical property of a material that allows coating of the material with an agarose layer, wherein the agarose layer binds to the material with sufficient strength to remain bound the material when the material (with the layer) is rinsed under tap water. Coupled to the hydrophilic surface of the carrier (and most typically coated onto the hydrophilic surface) is at least one light-blocking matrix layer that comprises a light-blocking agent, wherein the amount of light blocking agent is effective to render the carrier optically inactive. Further coupled to the light blocking matrix layer (and most typically coated onto light blocking matrix layer) is a coupling matrix layer, wherein the coupling matrix layer comprises a cross-linking agent that is physically suspended in the coupling matrix layer (and which may be covalently coupled to the coupling matrix layer). A plurality of sensing elements (with each of the plurality of sensing elements having a capture portion that binds to the cross-linking agent) is bound to the cross-linking agent in the coupling matrix layer in predetermined positions, and a modification matrix layer is coupled to the coupling matrix layer (and most typically coated onto the coupling matrix layer), wherein the modification matrix layer provides at least one of a chromatographic function, a light absorbing function, a penetration delay function, and an assay function.

With respect to the matrix layers, the same considerations as already described above apply. However, it is especially preferred that suitable light-blocking matrix layers, coupling matrix layer, and/or modification matrix layer comprise agarose at a concentration of about 1% by weight to about 5% by weight.

Figure 11:
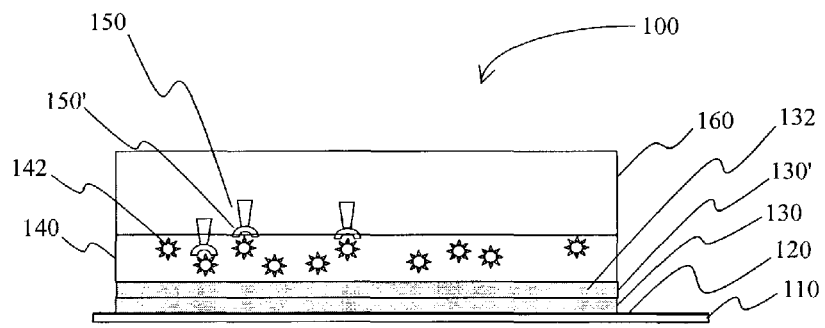
FIG. 11 is a cross-sectional view of another contemplated biochip comprising a modification matrix layer.

An exemplary biochip 100 is depicted in FIG. 11 in which a carrier 110 has a hydrophilic surface 120 (e.g., that is coated onto at least one surface of the carrier). Two light-blocking matrix layers 130 and 130' are successively coated onto the hydrophilic surface 120, wherein both of the light-blocking layers include a light blocking agent 132. Coated onto the light-blocking layer 130' is a coupling matrix layer 140 that includes cross-linking agent 142 that is optionally covalently bound to the coupling matrix layer 140. Sensing elements 150 include a capture portion 150' that binds to the cross-linking agent 142, wherein the sensing elements 150 are bound to the cross-linking agent 142 in the coupling matrix layer 140 in predetermined positions. Coated onto the coupling matrix layer 140 is modification matrix layer 160 that in this example provides a hydrophobic barrier that allows penetration of hydrophobic analytes (not shown) to the sensing elements 150 and prevents hydrophilic analytes (not shown) from penetrating to the sensing elements 150.

Of course it should be recognized that the modification matrix layer may provide numerous chromatographic functions other than a hydrophobic barrier. Among other chromatographic functions, suitable functions include size exclusion chromatography (e.g., molecular sieving (i.e., small molecules permeate modification matrix layer faster), or size separation (i.e., large molecules permeate modification matrix layer faster)), affinity chromatography (e.g., protein based affinity markers (e.g., antibody mediated, receptor mediated), small molecule mediated (e.g., ligands, substrates, cofactors), and metal-affinity mediated (e.g., Ni-chelates)), and ion exchange chromatography (e.g., cation and/or anion exchange). Chromatographic characteristics may be incorporated by numerous methods into the modification matrix layer (e.g., via chemical modification of the agarose to include ligands, proteins, anionic or cationic groups, or by inclusion of chromatographic material, etc), and all known methods are considered suitable for use herein.

Moreover, modification matrix layers may further include an optical filtering function (e.g., filtering of incident or emitted light), wherein the filtering may remove selected spectral ranges, or wherein the modification layer may act as a high-pass or low-pass filter. There are numerous chromogenic agents suitable for filtering incident or emitted light known in the art, and all of such agents may be dissolved, dispersed, or covalently bound to the modification matrix layer. Alternatively, the modification matrix layer may also be employed to control the time an analyte will require to reach the sensing elements (time delay), or determine the time in which the analyte has contact with the sensing element (e.g., via control of diffusion). Time delay or diffusion control may be achieved by a concentration gradient in the agarose (e.g., linear increasing top to bottom, or by layering several layers with different agarose concentration [low concentration-high concentration-low concentration]).

In still further contemplated aspects, the modification matrix layer may provide an the assay function. For example, contemplated assay functions include providing a substrate for an enzymatic assay (e.g., via dissolving a substrate in the matrix), providing a co-substrate for an enzymatic assay (e.g., via dissolving a co-substrate in the matrix), providing an enzyme for an enzymatic assay (e.g., via covalently coupling the enzyme to the modification matrix layer), and providing a chromogenic substrate for an enzymatic assay (e.g., via dissolving the chromogenic substrate in the matrix). Thus, it should be recognized that contemplated biochips not only include an analyte binding function, but may further include at least one additional non-analyte-binding function (e.g., include a functional element of the assay, include an element that modifies an assay, or includes an element that modifies the readout of the assay).

In still further contemplated aspects, the modification matrix layer may also include both hydrophilic and hydrophobic areas (e.g., checker board type distribution, or stripe wise distribution). Such bifunctional areas may be particularly advantageous when a substrate or analyte needs to be partitioned into predetermined areas of the biochip.

Furthermore, where desirable, a base matrix layer (not shown) may advantageously be included between the hydrophilic surface and the light-blocking matrix layer to reduce surface unevenness of surface of the carrier. Reduction in surface unevenness may be particularly desirable where the biochip is analyzed using a confocal microscope. Thus, in contemplated configurations a plurality of analytes in a plurality of positions on the biochip may be measured without recalibrating the focal plane.

Figure 12:
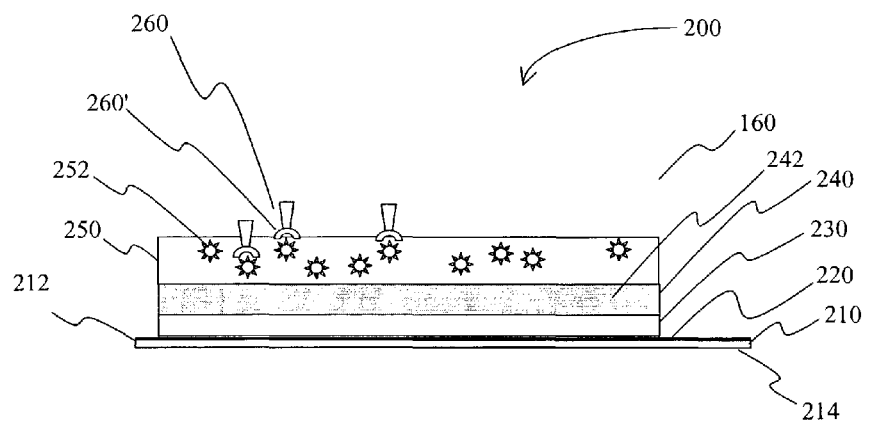
FIG. 12 is a cross-sectional view of a further contemplated biochip comprising a base matrix layer.

A further exemplary biochip 200 is depicted in FIG. 12 in which a carrier 210 has a first surface 212 and second surface 214, and wherein at least one of the first and second surfaces is hydrophilic or wherein the first surface has a hydrophilic coating 220. A base matrix layer 230 is coupled to the hydrophilic coating, and a light-blocking matrix layer 240 is coupled to the base matrix layer and further comprises a light-blocking agent at a concentration effective to render the carrier 210 optically inactive. A coupling matrix layer 250 is coupled to the light-blocking matrix layer 240, and a cross-linking agent 252 is physically suspended in the coupling matrix layer 250, wherein the cross-linking agent 252 is optionally covalently coupled to the coupling matrix layer 250. Sensing elements 260 have a capture portion 260' that binds to the cross-linking agent 252, and the sensing elements are bound to the cross-linking agent in the coupling matrix layer in predetermined positions.

It is especially preferred that in such configurations at least one of the base layer, the light-blocking matrix layer, and the coupling matrix layer comprises an additive, and especially suitable additives include a buffer, a detergent, a humectant, and a light-blocking agent. Furthermore, with respect to the sensing elements it is generally preferred that the sensing elements are coupled to the coupling matrix layer via droplet deposition of liquid droplets (e.g., via pin spotter, bubble printing, etc.) having a diameter of between 20 and 1000 micrometer to form a corresponding plurality of sensing element spots. It should be particularly noted that such deposition is significantly facilitated by (a) providing a multi-layer structure to reduce surface unevenness and (b) inclusion of an additive that reduces surface tension, reduces surface charge effects, and/or reduces changes in hydrations. Moreover, it is generally preferred that the light-blocking agent is present at a concentration to reduce a signal-to-noise ratio when an optical detection of a signal from the biochip is employed. With respect to the layers, light-blocking agents, additives, cross-linking agents, and sensing elements the same considerations as described above apply.

Figure 13:
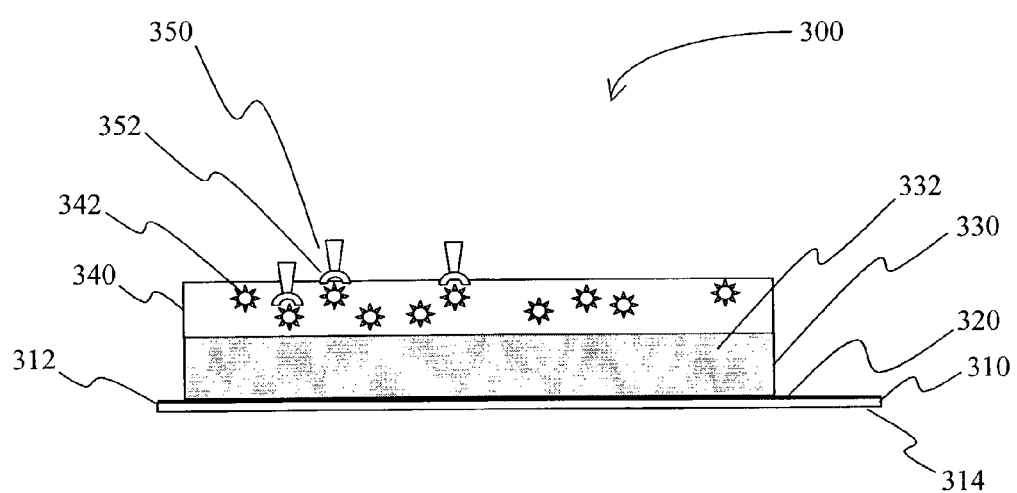
FIG. 13 is a cross-sectional view of yet another contemplated biochip according to the inventive subject matter.

In a still further preferred aspect of the inventive subject matter, a biochip 300 may have a configuration as depicted in FIG. 13 in which a carrier 310 has a first and a second surface, 312 and 314, respectively, and in which a hydrophilic coating 320 is coupled to the first surface of the carrier. At least one light-blocking matrix layer 330 comprising a light-blocking agent 332 is coupled to the hydrophilic coating 320, wherein the light-blocking matrix layer 330 is effective to render the carrier optically inactive. A coupling matrix layer 340 is further coupled to the light-blocking matrix layer 330, and a cross-linking agent 342 is physically suspended in the coupling matrix layer 340, wherein the cross-linking agent 342 is optionally covalently coupled to the coupling matrix layer 340. A plurality of sensing elements 350 having a capture portion 352 that binds to the cross-linking agent is bound to the cross-linking agent 342 in the coupling matrix layer 340 in predetermined positions, wherein the plurality of sensing elements 350 are coupled to the coupling matrix layer 340 via droplet deposition of liquid droplets having a diameter of between 20 and 1000 micrometer to form a corresponding plurality of sensing element spots. Again, with respect to the layers, light-blocking agents, additives, cross-linking agents, and sensing elements the same considerations as described above apply.

EXAMPLES

The following examples are offered by way of illustration, and not by way of limitation.

Example 1

Experiment 1—Marker in Matrix Coating

This experiment demonstrated that an aqueous matrix adheres to the carrier, the first side of which having been rendered hydrophilic, and does not interfere with the colormentric event of a fluorescent marker. Optically pure, 100 micron thick Mylar (Dupont Corp., Cat. No, P4C 1 A) with a gelatin coating was obtained from the Dupont Corporation. A solution of standard agarose in water was prepared as described below. Cy3 marker (NEN Life Sciences) was added to the solution and mixed thoroughly yielding a uniform suspension. The Cy3-agarose solution was then spread evenly over the carrier using a Leneta Wire-Cator (BYK-Gardner Corporation) as described below. The coating was then allowed to cool. Using a Bio-Rad MRC-1024 Cofocal Microscope and Omnichrome 643 100 Kr—Ar laser (Bio-Rad Laboratories, Hercules, Calif.), a 200 micron area of the coated carrier was excited with a wavelength of 550 nm. The microscope detected an image over every 200 micron area of the surface of the matrix using a detection (emission) setting of 570 nm.

Experiment 2—Concentration of Light Blocking Agent

This experiment determined the amount of light blocking agent required to render the carrier optically inactive. A 2% solution of standard agarose in water and 6 gm of iron oxide was prepared as described below. The Cy3-agarose coated carrier from experiment 1 was then coated to make a 200 micron layer of the iron oxide-agarose solution and allowed to cool. Using the same procedure from Experiment 1, an image was detected over every 200 micron area of the surface of the matrix. The iron oxide-agarose coating step was repeated five times on the same carrier until no image was detected on the surface of the matrix using the confocal microscope of experiment 1. The total concentration of iron oxide which completely blocked the Cy3 image identified the amount of light blocking agent needed to render the carrier optically inactive. It should be understood that one of skill in the art can determine the amount of any light blocking agent required to render a carrier optically inactive using the above procedure.

Experiment 3—Formation of a Stage for Building a Platform

This experiment was performed to show that the total amount of light blocking agent required to render the carrier optically inactive could be applied in a single coating, thereby forming the stage for building a platform. The procedure of experiment 2 was duplicated using a single layer of iron oxide-agarose solution, at the concentration identified in experiment 2. Again, using the confocal microscope and laser of experiment 1, the Cy3 image was completely blocked. The experiment was then repeated utilizing a different piece of Mylar film to verify the results.

Experiment 4—Sensing Element Bound to the Matrix

As used hereinafter,

Oligo A—SEQ ID: 1, biotinylated at 5' position; Cy3 labeled at 3' position.

Oligo B—SEQ ID: 1, biotinylated at 5' position; not labeled at 3' position.

Oligo C—SEQ ID: 2, Cy3 labeled at 3' position.

Oligo D—SEQ ID: 2, biotinylated at 5' position; not labeled at 3' position.

Oligo E—SEQ ID: 2, not labeled at 3' position.

Oligo F—SEQ ID: 3, Cy3 labeled at 3' position.

SEQ ID: 1 = 5'-AAT CCA GAT ATA GTC ATC TAG CAA TAC A-3'

SEQ ID: 2 = 5'-TTA GCT CGA CTC AGG GAT CCG GAT TGT ATT GCT AGA-3'

SEQ ID: 3 = 5'-ATC CGG ATC CCT-3'

This experiment was performed to show that sensing elements adhere to the top surface of the matrix coating containing cross-linking agents. A 2% solution of standard agarose in water with 2.25% strepavidin was prepared as described below. The strepavidinagarose solution was then coated onto the first side of a clean (i.e., as delivered from Dupont Corporation) piece of carrier. An aliquot of Oligo A (NEN Life Science Products) was then deposited over the surface of the matrix and allowed to cross-link. Using the confocal microscope and laser of experiment 1, an image was detected over every 200 micron area of the surface of the matrix.

Experiment 5—Adhesion of Sensing Element to the Matrix

This experiment was performed to show that the heterobifunctional cross-linking bond between the sensing elements and the surface of the matrix is not affected by subsequent washes with deionized water. The procedure of experiment 4 was repeated. However, the coated carrier was repeatedly washed with deionized water following the addition of Oligo A to verify that the sensing element was bound essentially irreversibly to the surface of the matrix. Using the confocal microscope and laser of experiment 1, an image was detected over every 200 micron area of the surface of the matrix.

Experiment 6—Light Blocking Agent

This experiment was performed to show that the light blocking agent disposed over the matrix containing a cross-linking system renders the carrier optically inactive. The solution of agarose in water with strepavidin from experiment 4 was coated onto the first side of a clean piece of carrier. Then the solution of light blocking agent in agarose from experiment 3 was coated over the initial matrix coating. Using the confocal microscope and laser of experiment 1, no image was detected.

Experiment 7—Formation of a Platform for Building a Biochip

This experiment was performed to show that a matrix coating, containing cross-linking agents, disposed over the light blocking agent has no affect on the light blocking agent's ability to render the carrier optically inactive. A standard solution of aldehydeactivated agarose, commercially available as NUFIX™ (glyoxyl agarose), was prepared with strepavidin, as described below. The procedure of experiment 6 was repeated. The NUFIX™ (glyoxyl agarose) solution was then coated over the light blocking agent and allowed to cool, thereby forming a platform for building a biochip. Using the confocal microscope and laser of experiment 1, no image was detected.

Experiment 8—Labeled Sensing Element Cross-Linked to a Platform

This experiment was performed to show that a fluorescently-labeled sensing element produces a detectable colorimetric effect (here: fluorescence) when bound to the top surface of a platform. The procedure of experiment 7 was repeated. Then an aliquot of Oligo A from experiment 4 was deposited over the surface of the matrix and allowed to cross-link. Using the confocal microscope and laser of experiment 1, an image was detected over every 200 micron area of the surface of the matrix.

Experiment 9—Unlabeled Sensing Element Produced No Image

This experiment was performed to show that an unlabeled sensing element bound to the surface of the matrix does not produce a colorimetric effect. The procedure of experiment 7 was followed using Oligo B (NEN. Life Science Products). Using the confocal microscope and laser of experiment 1, no image was detected.

Experiment 10—Detecting a Reporter Probe Bound to a Sensing Element

This experiment was performed to show that a fluorescently-labeled analyte (e.g., nucleic acid) that hybridizes to a sensing element bound to the surface of the matrix produces a colorimetric effect. The procedure of experiment 9 was repeated. An aliquot of Oligo C (NEN Life Science Products), which is partially complementary to Oligo A, was then deposited over the surface of the matrix and allowed to hybridize with Oligo B. This experiment was performed in triplicate, allowing Oligo C to hybridize for 4 hours, 8 hours, and overnight. Using the confocal microscope and laser of experiment 1, images were detected over every 200 micron area of the surfaces of each of the matrices.

Experiment 11—Formation of a Biochip

This experiment was performed to show that unlabeled nucleic acid sensing elements spotted onto the surface of the matrix do not produce a colorimetric effect. A 210 micron pin was obtained from TeleChem International, Inc., Sunnyvale, Calif. A corresponding 4-spot metal spotting block was machined at a local metal fabricating shop such that the weight of the pin spotter determines the amount of oligo that is deposited. The procedure of experiment 7 was repeated. Two spots of Oligo B from experiment 9 were then spotted onto the surface of the matrix. Using the confocal microscope and laser of experiment 1, no image was detected. The device was then washed with deionized water and placed in the confocal microscope for another reading. No image was detected.

Experiment 12—Detecting Reporter Probes Bound to Spotted Sensing Elements on a Biochip This experiment was performed to show that the spotted nucleic acid sensing elements bound to the surface of the matrix remain fixed in position and do not migrate over the surface of the matrix. Further, this experiment demonstrated that stray light impinging upon the device from surfaces other than the top did not affect the light blocking agent's ability to render the carrier optically inactive. The procedure of experiment 11 was repeated. An aliquot of Oligo C (NEN Life Science Products) was then deposited over the surface of the matrix and allowed to hybridize with Oligo B, which was spotted onto the surface of the matrix. After washing with deionized water, two distinct spot images were detected on the surface of the matrix using the confocal microscope and laser of experiment 1. Finally, stray light was allowed to contact the bottom surface of the carrier during another reading with the confocal microscope. The stray light did not affect upon the images detected.

Experiment 13—Nucleic Acid Sandwich Hybridization Asses Performed on the Biochip A standard nucleic acid sandwich hybridization assay was carried out on the biochip of the invention. The procedure of experiment 11 was repeated. An aliquot of Oligo E (NEN Life Science Products) was then deposited over the surface of the matrix and allowed to hybridize with Oligo B, which was spotted onto the surface of the matrix. After washing with deionized water, an aliquot of Oligo F was deposited over the surface of the matrix and allowed to hybridize with Oligo E. After washing with deionized water, two distinct spot images were detected on the surface of the matrix using the confocal microscope and laser of experiment 1. One of ordinary skill in the art would refer to Sambrook, J. et al. vol. 1-3, *Molecular Cloning, A Laboratory Manual*, 1989 for a detailed description of nucleic acid sandwich hybridization assays.

Example 2

Fabricating the Stage

Preparation of Reagents

2% Agarose—Bottom Level of Matrix
1. Measure 20 grams of dry agarose and place into 2 liter beaker
2. Add 1 liter of deionized water and place on hot plate to slowly bring to a boil
3. Stir occasionally with a glass stir rod until all of the agarose is completely melted
4. Turn off heat and allow mixture to cool to room temperature with aluminum foil cover over beaker to keep out dust.
5. After hardening, the agarose should be labeled and can be tightly sealed and stored in a refrigerator for later use.

2% Agarose with Iron Oxide (Light Blocking Agent)—Middle Level of Matrix
1. Measure 20 grams of dry agarose and place into 2 liter beaker
2. Add 500 ml of deionized water and place on a hot plate to slowly bring to a boil
3. Stir occasionally with a glass rod until all of the agarose is completely melted
4. Measure 6 grams of iron oxide into container and mix until completely and homogeneously dispersed
5. In a second 2 liter beaker, warm about 750 ml of deionized water to about 80° C.
6. Bring the volume of the iron oxide preparation up to 1 liter by adding 80° C. deionized water. Mix the dispersion until smooth and completely dispersed
7. Turn off heat and allow mixture to cool to room temperature with an aluminum foil cover over the beaker to keep out dust.
8. After hardening, the agarose should be labeled and can be tightly sealed and stored in a refrigerator for later use.

Buffer A
1. Add 100 ml of deionized water to a 250 ml Erlenmyer flask with a small stir bar
2. Place on a magnetic stirrer and stir slowly
3. Add 0.01 moles of Hepes free acid and allow to dissolve
4. Measure pH and adjust to 7.4±0.05 using either 0.5 molar NaOH or 0.5 molar HCl
5. Add 0.02 grams of TWEEN-20 (polyoxyethylenesorbitan monostearate)
6. Bring volume in the flask up to 200 ml using deionized water and stir to dissolve contents completely Buffer B
1. Add 100 ml of deionized water to a 250 ml Erlenmyer flask with a small stir bar
2. Place on a magnetic stirrer and stir slowly
3. Add 0.01 moles of methane-ethane sulphonic acid (MES) and allow to dissolve completely
4. Measure pH and adjust to 6.8±0.05 using either 0.5 molar NaOH or 0.5 molar HCl
5. Add 0.03 grams of TWEEN-20 (polyoxyethylenesorbitan monostearate)
6. Bring volume in the flask up to 200 ml using deionized water and stir to dissolve contents completely.

Depositing or Coating Matrix onto Carrier

By way of example, but not limitation, a method for depositing the matrix coating onto the first side of the carrier involves quickly dispensing a melted material, suitable for use as a matrix coating, onto the carrier. Just after the solution spreads over the surface of the carrier, a Leneta Wire-Cator or a Bird Film applicator capable of delivering a prescribed volume per square meter is drawn down the carrier to spread liquified matrix material evenly over the surface of the carrier. Such coating applicators are commercially available from BYK-Gardner Corporation. The carrier sat at room temperature until the coating was dry. Various other useful coating techniques are known to those skilled in the art.

By way of further example, but not limitation, another method for depositing or coating the first side of the carrier involves industrial machinery. Flexible carrier materials are commercially available from sources such as Dupont Corporation. A flexible material is rolled onto a core suitable for loading onto said industrial machinery. The machinery draws the carrier material under a series of warmers, coaters and driers, depending on the product desired. Standard film coating techniques are known to those of skill in the art.

Bottom Level of Matrix
1. Heat about 1.5 liters of water in a beaker until approximately 60° C. and pour into a 1 liter graduated cylinder. Place a wire wound coating rod capable of delivering a 50 ml per square meter coverage into the cylinder in order to warm it.
2. Cut a piece of 5.25 inch gelatin-coated mylar (polyester) carrier about 20 inches long and tape one short edge onto a flat surface such as a lab bench. Be certain that the hydrophilic side (gelatin coated side) is facing up. This can be determined by simply breathing on each side. The hydrophilic side will fog up with breath.
3. Use a spatula and measure 10 grams of 2% agarose into a conical centrifuge/culture tube
4. Add 10 ml of Buffer A.

5. Place the loosely capped tube into a microwave and heat on high in 20 second increments until melted. Be careful not to boil over the tube.
6. Place the tube in the water bath at 50° C. and hold until needed
7. Working quickly, remove the wire wound rod from the warm water and dry with a paper towel. Place at the top of the carrier.
8. Remove the culture tube from the water bath and pour about ½ of the contents overt' coating rod. Just after solution spreads onto the carrier, lightly grab the rod and dray down the coating.
9. Allow the coated carrier to sit at room temperature for 20 minutes. It can then be allowed to air dry for at least 2 hours.

Middle Level of Matrix
1. Heat about 1.5 liters of water in a beaker until approximately 60° C. and pour into a 1 liter graduated cylinder. Place a wire wound coating rod capable of delivering a 200 ml per square meter coverage into the cylinder in order to warm it.
2. Tape down the carrier (upon which the bottom matrix level has been deposited or coated), coating side up, onto a flat surface such as a lab bench.
3. Use a spatula and measure 10 grams of 2% agarose, with Iron Oxide into a conical centrifuge/culture tube.
4. Add 10 ml of Buffer B
5. Place the loosely capped tube into a microwave and heat on high in 20 second increments until melted. Be careful not to boil over the tube.
6. Place the tube in the water bath at 50° C. and hold until needed
7. Working quickly, remove the wire wound rod from the warm water and dry with a paper towel. Place at the top of the coated carrier.
8. Remove the culture tube from the water bath and pour about ½ of the contents over the coating rod. Just after solution spreads onto the carrier, lightly grab the rod and draw down the coating.
9. Allow the coated carrier to sit at room temperature for 20 minutes. It can then be allowed to air dry for at least 2 hours.

Example 3

Fabricating the Platform

Preparation of Reagents

2% NUFIX™ (Glyoxyl Agarose)—Top Level of Matrix
1. Measure 20 grams of NUFIX™ (glyoxyl agarose) and place into a 2 liter beaker
2. Add 1 liter of deionized water and place on a hot plate to slowly bring to a boil
3. Stir occasionally with a glass rod until all of the agarose is completely melted
4. Turn off heat and allow mixture to cool to room temperature with an aluminum foil cover over the beaker to keep out dust.
5. After hardening, the agarose should be labeled and can be tightly sealed and stored in a refrigerator for later use.

Buffer C
1. Add 100 ml of deionized water to a 250 ml Erlenmyer flask with a small stir bar
2. Place on a magnetic stirrer and stir slowly
3. Add 1.0 mM of dibasic sodium phosphate
4. Measure pH and adjust to 5.8±0.05 using either 0.5 molar NaOH or 0.5 molar HCl
5. Bring volume in the flask up to 200 ml using deionized water and stir to dissolve contents completely Buffer D
1. Add 100 ml of deionized water to a 250 ml Erlenmyer flask with a small stir bar
2. Place on a magnetic stirrer and stir slowly
3. Add 2.0 mM of dibasic sodium phosphate
4. Measure pH and adjust to 7.0±0.05 using either 0.5 molar NaOH or 0.5 molar HCl
5. Bring volume in the flask up to 200 ml using deionized water and stir to dissolve contents completely.

Depositing Cross-Linking System onto Stage to Form Platform

Top Level of Matrix
1. Use a spatula and measure 10 grams of 2% NUFIX™ (glyoxyl agarose) into a conical centrifuge/culture tube.
2. Add 2 ml of Buffer C.
3. Place the loosely capped tube into a microwave and heat on high in 20 second increments until melted. Be careful not to boil over the tube.
4. Place the tube in the water bath at 50° C. and hold until needed.
5. In a 10 ml disposable culture tube, prepare 3.0 ml of a 10 mg/ml solution of Strepavidin in Buffer C.
6. Warm the Strepavidin solution to 50° C. in a water bath.
7. After the Strepavidin solution has warmed, remove 2.5 ml and add it to the tube from step 4 above. Mix the 14.5 ml NUFIX™ (glyoxyl agarose)/Strepavidin solution and incubate for 2 hours in a 50° C. water bath.
8. While the NUFIX™ (glyoxyl agarose)/Strepavidin solution reacts, prepare the following:
   8a. In a 10 ml disposable conical tube, add 1 ml of 1.33M sodium cyanoborohydride to 1 ml Buffer D solution;
   8b. In a second 10 ml disposable conical tube, add 1.5 ml of 300 mM histidine to 1.5 ml Buffer D solution;
9. After the 2 hour incubation of the NUFIX™ (glyoxyl agarose)/Strepavidin solution, add 1.67 ml of 300 mM histidine. Mix thoroughly and incubate at 50° C. for 1 hour.
10. After 1 hour of incubation, add 0.29 ml of 1.33M sodium cyanoborohydride. Add 0.04 gm TWEEN-20 (polyoxyethylenesorbitan monostearate) and mix thoroughly and react for 1 hour at 50° C. Do not cap the tube tightly as hydrogen gas may be produced. Allow tube to vent.
11. Heat about 1.5 liters of water in a beaker until approximately 60° C. and pour into a 1 liter graduated cylinder. Place a wire wound coating rod capable of delivering a 200 ml per square meter coverage into the cylinder in order to warm it.
12. Tape down the stage, coating side up, onto a flat surface such as a lab bench.
13. Working quickly, remove the wire wound rod from the warm water and dry with a paper towel. Place at the top of the coated carrier.
14. Remove the culture tube from the water bath and pour about ½ of the contents over the coating rod. Just after solution spreads to onto the carrier, lightly grab the rod and draw down the coating.

15. Allow the coated stage to sit at room temperature for 20 minutes. It can then be allowed to air dry for at least 2 hours.

Example 4

Preparation of the Biochip

Recent development of new technologies for synthesizing or depositing nucleic acids on substrates at very high densities have allowed the miniaturization of nucleic acid arrays yielding increased experimental efficiency and information content. (Lockhart & Winzeler, Genomics, Gene Expression and DNA Arrays, Functional Genomics, 405:6788, June 2000, 827-35). The methods disclosed herein are easily adaptable to an automated manufacturing process ("Microarray Biochip Technology," Ed. Mark Schena, Eaton Publishing, Natick, Mass., 2000); and reference to standard film coating procedures available from the film or film coating industry.

Commonly used techniques in the art are available for depositing sensing elements onto the surface of the platform. The sensing elements are typically deposited in droplets with a spot diameter ranging from about 20 to 1000 μm, preferably 120 μm spaced about 200 μm apart. The platform is suitable for spotting by all contact and non-contact methods. Spotting devices and techniques known in the art include, but are not limited to, syringe-solenoid, solid pin replicator, quill and split pin, tweezer, PIN-AND-RING™, and jetting and piezoelectric pumps. One of ordinary skill in the art would refer to "*Microarray Biochip Technology*," Ed. Mark Schena, Eaton Publishing, Natick, Mass., 2000, for a detailed description of spotting techniques.

Example 5

Use of the Biochip

Using the biochips or microarrays of the invention, one can conduct applications in the fields of genomics and proteomics such as pharmacogenomics, gene expression, mutation analysis, compound screening, toxicology, Single Nucleotide Polymorphism (SNPs) analysis, Short Tandem Repeats (STRs) and molecular diagnostics. The biochip of the invention is easily adaptable to massively parallel experimentation in these applications. One of skill in the art will employ conventional biochemistry, molecular biology and recombinant DNA techniques, antigen retrieval techniques, as well as techniques and protocols in molecular diagnostics referred to herein, and, to the extent possible, incorporated by reference herein. Such techniques are explained fully in the literature.

The embodiments of the invention are not meant to be restricted by the above disclosure, but only by the claims below. Nonetheless, the present invention finds use as a platform for a variety of different detection methods. The detection modes include, but are not limited to reflection, fluorescence, phosphorescence, absorption, magnetism, polarization, chemiluminescence, electricity, conductivity, resistivity, colorimetricity, piezo-electricity, and radioactivity.

Utilizing the biochips of the invention as microarrays, one can conduct massively parallel experiments in applications as diverse as, pharmacogenomics, gene expression, compound screening, toxicology, Single Nucleotide Polymorphism (SNPs) analysis, Short Tandem Repeats (STRs) and molecular diagnostics. The biochip finds use in massively parallel experimentation in these applications. Embodiments of the biochip of the invention include arrays of peptides, proteins, small molecules, mRNAs, cDNAs, clones, tissues, and cells disposed on the biochip as sensing elements. In short, the devices and methods of the invention are advantageously used in exploring genome data, protein function in relation to genome function (proteomics), genetic determinants (Nature Insight, vol. 405, no. 6788, 15 Jun. 2000).

Further embodiments involve adapting the invention for use in a cartridge, said cartridge being used in an automated detection system based on fluorescence-detection methods.

What is claimed is:

1. A biochip comprising:

a carrier, optionally with a hydrophilic surface;

at least one light-blocking matrix layer comprising at least one of a gelatin, a polyvinyl alcohol, a polyvinyl pyrrolidone, an agarose, and a polyacrylamide, and further comprising a light-blocking agent, wherein the at least one light-blocking matrix layer is coupled to the carrier and the optional hydrophilic surface and is effective to render the carrier optically inactive;

a coupling matrix layer coupled to the light-blocking matrix layer, and a cross-linking agent suspended within the coupling matrix layer, wherein the cross-linking agent is optionally covalently coupled to the coupling matrix layer;

a plurality of distinct nucleic acids, each of the plurality of nucleic acids having a capture portion that non-covalently binds to the cross-linking agent, and wherein the distinct nucleic acids are non-covalently bound to the cross-linking agent in the coupling matrix layer at respective distinct and predetermined positions on the coupling matrix layer;

an optional modification matrix layer coupled to the coupling matrix layer, wherein the modification matrix layer provides at least one of a chromatographic function, a light absorbing function, a penetration delay function, and an assay function; and wherein the light-blocking matrix layer is disposed between the carrier and the coupling matrix layer, and wherein the coupling matrix layer is disposed above the light blocking matrix layer and below the optional modification matrix layer.

2. The biochip of claim 1 wherein at least one of the light-blocking matrix layer, the coupling matrix layer, and the modification matrix layer comprises agarose at a concentration of about 1% by weight to about 5% by weight.

3. The biochip of claim 2 wherein the chromatographic function is selected from the group consisting of size exclusion chromatography, affinity chromatography, and ion exchange chromatography.

4. The biochip of claim 2 wherein the light absorbing function is selected from the group consisting of filtering of an incident light and filtering of an emitted light.

5. The biochip of claim 2 wherein the assay function is selected from the group consisting of providing a substrate for an enzymatic assay, providing a co-substrate for an enzymatic assay, providing an enzyme for an enzymatic assay, and providing a chromogenic or luminogenic substrate for an enzymatic assay.

6. The biochip of claim 2 further comprising a base matrix layer that is disposed between the hydrophilic surface and the light-blocking matrix layer.

7. The biochip of claim 2 wherein the light blocking agent is iron oxide and wherein the cross-linking agent is avidin or streptavidin.

8. A biochip comprising:

a carrier with a first and second surface;

a base matrix layer comprising at least one of a gelatin, a polyvinyl alcohol, a polyvinyl pyrrolidone, an agarose, and a polyacrylamide, wherein the base matrix layer is coupled to the first surface;

a light-blocking matrix layer coupled to the base matrix layer and comprising at least one of a gelatin, a polyvinyl alcohol, a polyvinyl pyrrolidone, an agarose, and a polyacrylamide, and further comprising a light-blocking agent, wherein the light-blocking matrix layer is coupled to the base matrix layer and is effective to render the carrier optically inactive;

a coupling matrix layer coupled to the light-blocking matrix layer, and a cross-linking agent suspended within the coupling matrix layer, wherein the cross-linking agent is optionally covalently coupled to the coupling matrix layer;

a plurality of distinct nucleic acids, each of the plurality of distinct nucleic acids having a capture portion that binds non-covalently to the cross-linking agent, and wherein the nucleic acids are bound to the cross-linking agent in the coupling matrix layer in respective distinct and predetermined positions on the coupling matrix layer;

wherein the light-blocking matrix layer is disposed between the carrier and the coupling matrix layer;

wherein at least one of the base layer, the light-blocking matrix layer, and the coupling matrix layer includes an additive selected from the group consisting of a buffer, a detergent, a humectant, and a light-blocking agent; and wherein the plurality of distinct nucleic acids are coupled to the coupling matrix layer such that they form a plurality of nucleic acid spots having respective diameters of between 20 and 1000 micrometer.

9. The biochip of claim 8 wherein at least one of the base matrix layer, the light-blocking matrix layer, and the coupling matrix layer comprise agarose at a concentration of about 1% by weight to about 5% by weight.

10. The biochip of claim 9 wherein the buffer is an ampholeric buffer, and wherein the light blocking agent is an iron oxide.

11. The biochip of claim 9 wherein the coupling matrix layer comprises aldehyde-activated agarose at a concentration of about 1% by weight to about 5% by weight.

12. The biochip of claim 11 wherein the cross-linking agent is avidin, streptavidin, or an antibody, and wherein the cross-linking agent is covalently coupled to the coupling matrix layer.

13. The biochip of claim 12 wherein the capture portion comprises a biotin.

14. The biochip of claim 9 wherein the carrier is a flexible and optically pure polymer film with a thickness of about 100 micrometers and further includes a gelatin coating as the hydrophilic coating.

15. The biochip of claim 9 wherein the additive is present in an amount effective to control surface irregularity of the coupling matrix layer, thereby allowing optical detection using a confocal microscope of a plurality of signals from a plurality of analytes bound to the plurality of nucleic acids without recalibration of the confocal microscope.

16. The biochip of claim 9 wherein the light-blocking agent is present at a concentration to increase a signal-to-noise ratio when an optical detection of a signal from the biochip is employed.

17. A biochip comprising:
a carrier with a first and second surface;
at least one light-blocking matrix layer comprising at least one of a gelatin, a polyvinyl alcohol, a polyvinyl pyrrolidone, an agarose, and a polyacrylamide, and further comprising a light-blocking agent, wherein the at least one light-blocking matrix layer is coupled to the carrier and is effective to render the carrier optically inactive;
a coupling matrix layer coupled to the light-blocking matrix layer, and a cross-linking agent suspended within the coupling matrix layer, wherein the cross-linking agent is optionally covalently coupled to the coupling matrix layer;
wherein the light-blocking matrix layer is disposed between the carrier and the coupling matrix layer;
a plurality of distinct nucleic acids, each of the plurality of nucleic acids having a capture portion that binds non-covalently to the cross-linking agent, and wherein the distinct nucleic acids are bound to the cross-linking agent in the coupling matrix layer in respective distinct and predetermined positions; and
wherein the plurality of nucleic acids are coupled to the coupling matrix layer such that they form a plurality of nucleic acid spots having respective diameters of between 20 and 1000 micrometer.

18. The biochip of claim 17 wherein at least one of the light-blocking matrix layer and the coupling matrix layer comprise agarose at a concentration of about 1% by weight to about 5% by weight, and wherein the light-blocking agent is present at a concentration to increase a signal-to-noise ratio when an optical detection of a signal from the biochip is employed.

19. The biochip of claim 18 wherein the carrier is a flexible and optically pure polymer film with a thickness of about 100 micrometers and further includes a gelatin, a polyvinyl alcohol, or a polyvinyl pyrrolidone coating as a hydrophilic coating.

20. The biochip of claim 18 further comprising a base matrix layer that is disposed between the carrier and the light-blocking matrix layer.

\* \* \* \* \*

SEQUENCE LISTING

```
<160> NUMBER OF SEQ ID NOS: 3

<210> SEQ ID NO 1
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic Oligonucleotide

<400> SEQUENCE: 1
aatccagata tagtcatcta gcaataca                                      28

<210> SEQ ID NO 2
<211> LENGTH: 36
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: Synthetic Oligonucleotide
```

-continued

```
<400> SEQUENCE: 2
ttagctcgac tcagggatcc ggattgtatt gctaga                                36

<210> SEQ ID NO 3
<211> LENGTH: 12
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(12)
<223> OTHER INFORMATION: Synthetic Oligonucleotide

<400> SEQUENCE: 3
atccggatcc ct                                                          12
```